United States Patent [19] [11] 4,221,801
Kuipers et al. [45] Sep. 9, 1980

[54] COMPOSITION FOR THE TREATMENT OF SOIL OR SEED AGAINST PHYTOPHAGOUS FUNGI

[75] Inventors: Johannes Kuipers; Hendrik Dolman, both of Weesp, Netherlands

[73] Assignee: Duphar International Research, Weesp, Netherlands

[21] Appl. No.: 965,215

[22] Filed: Nov. 30, 1978

[30] Foreign Application Priority Data

Dec. 1, 1977 [NL] Netherlands .......................... 7713267

[51] Int. Cl.$^2$ ........................... A01N 9/12; A01N 9/20
[52] U.S. Cl. .................................................... 424/270
[58] Field of Search .......................................... 424/270

[56] References Cited

U.S. PATENT DOCUMENTS

| | | | |
|---|---|---|---|
| 3,736,329 | 5/1973 | Verge et al. | 424/270 |
| 3,740,400 | 6/1973 | Berkelhammer et al. | 424/270 |
| 4,006,241 | 2/1977 | Strehlke et al. | 424/270 |

FOREIGN PATENT DOCUMENTS 2014527  6/1968  France ...................................... 424/270

OTHER PUBLICATIONS

J. Med. Chem. 12 303–306 (1969), Henry.

*Primary Examiner*—Douglas W. Robinson
*Attorney, Agent, or Firm*—Norman N. Spain

[57] ABSTRACT

The invention relates to a composition against phytophagous micro-organisms, comprising 2-cyano-5-nitro-thiazole. Infections by phytophagous micro-organisms in agriculture and horitculture can be prevented by treating the seed prior to sowing or the soil destined for sowing or planting with the composition in a dosage of from 100 to 600 mg of active substance per kg of seed and from 2 to 100 kg of active substance per hextare, respectively.

3 Claims, No Drawings

COMPOSITION FOR THE TREATMENT OF SOIL OR SEED AGAINST PHYTOPHAGOUS FUNGI

The invention relates to a composition for the treatment of soil or seed against phytophagous microorganisms, as well as to a method of preventing infections by said micro-organisms in agriculture and horticulture.

Phytophagous soil organisms (soilborne diseases), particularly pytogenic fungi for example Pythium spp. and *Rhizoctonia solani*, may seriously infest seedlings or young plants.

It has now been found that a composition, which, in addition to a liquid or solid inert carrier material, comprises as active substance 2-cyano-5-nitro-thiazole, provides a good protection to seedlings and plants against infestation by said soil organisms.

For this purpose, the soil destined for sowing or planting, or the seed itself, the latter being usually preferred for reasons or efficiency, is treated with a composition according to the invention.

Such a composition also proves to be particularly active against phytophagous micro-organisms which are carried by the seed (seedborne diseases), particularly phytogenic fungi for example *Pyrenophora graminea* on barley, Fusarium spp. on wheat, *Tilletia caries* on wheat, *Ustiliago avenae* on oats, and *Phoma betae* on beets.

An efficient protection against the last-mentioned micro-organisms is obtained by treating the seed prior to sowing with a composition according to the invention.

The active substance present in the composition, namely 2-cyano-5-nitro-thiazole has already been described many times in literature, for example in J. Med. Chem. 12 303 (1969). In said literature the compound is used as a starting material for the synthesis of other compounds. An activity as found in the present invention is not known.

German Patent Application (Offenlegungsschrift) 2131888 ascribes a fungicidal activity to 2-carbonamide-5-nitro-thiazole. However, compared with the 2-cyano-5-nitro-thiazole to be used according to the invention, said compound proves to have only a small activity when used against phytophagous micro-organisms, as will become apparently hereinafter from the specific examples.

A composition according to the invention is prepared by mixing the active substance with a solid carrier material or dissolving or dispersing it in a liquid carrier material, possibly combined with auxiliary substances, such as emulsifiers, wetting agents, dispersing agents and stabilisers.

Examples of compositions according to the invention are aqueous dispersions, oily solutions and oily dispersions, solutions in organic solvents, pastes, dusting powders, dispersible powders, miscible oils, granules, invert emulsions, aerosol compositions and smoke generating candles.

Dispersible powder, pastes and miscible oils are compositions in concentrate formed which are diluted with water prior to or during use.

The invert emulsions and solutions in organic solvents may also used in air application, particularly when large areas are to be treated with a comparatively small quantity of composition. The invert emulsions may be prepared shortly prior to or even during spraying in the spraying apparatus by emulsifying water in an oily solution or an oily dispersion of the active substance.

As solvents for the active substance there may be used organic solvents which are not detrimental to the seed or the young plants, for example, monovalent or multivalent alcohols, for example ethanol or oxitoles, or aromatic hydrocarbons.

A few forms of the compositions of the invention will be now described in greater detail by way of example.

Granular compositions are prepared, for example, by taking up or dispersing the active substance in a solvent thinner and impregnating the resulting solution or suspension, if desired in the presence of a binder, on granular carrier materials, for example, porous granules (for example, pumice and attaclay), mineral non-porous granules (sand or ground marlow) organic granules (for example, dried coffee ground and tobacco stems and corncob).

A granular composition may alternatively be manufactured by compressing the active substance together with powdered minerals in the presence of lubricating agents and binders and disintegrating and sieving the products to the desired grain size.

Another possibility for preparing granules is by using the glomulation technique.

Dusting powders can be obtained by intimately mixing the active substance with an inert solid carrier material, for example talc.

Dispersible powders are prepared by mixing from 10 to 80 parts by weight of a solid inert carrier, for example kaolin, dolomite, gypsum, chalk, bentonite, attapulgite, colloidal $SiO_2$ or mixtures of these and similar substances, with from 10 to 80 parts by weight of the active substance, from 1 to 5 parts by weight of dispersing agent, for example, the lignin sulphonates known for this purpose or alkylnaphthalene sulphonates, and preferably also from 0.5 to 5 parts by weight of a wetting agent for example, fatty alcohol sulphates, alkylaryl sulphonates, naphthalene sulphonate, alkylpolyoxyethylenes or alkylarylpolyoxyethylenes.

For the preparation of miscible oils the active compound is dissolved or finely dispersed in a suitable solvent which preferably is water-immiscible and an emulsifier is added to this solution. Suitable solvents are, for example, xylene, toluene, petroleum distillates which are rich in aromates, for example solvent naphtha, distilled tar oil and mixtures of these liquids. As emulsifiers there may be added, for example alkylphenoxypolyglycol ethers, polyoxyethylene sorbitan esters of fatty acids or polyoxyethylene sorbitol esters of fatty acids. The concentration of the active compound in said miscible oils is not restricted to narrow limits and may vary, for example, between 2 and 50% by weight. In addition to a miscible oil, there also may be employed as a liquid and highly concentrated primary composition, a solution of the active substance in a readily water-miscible liquid, for example a glycol or glycolester, to which solution a dispersing agent and if desired a wetting agent are added. Upon diluting with water shortly prior to or during spraying, an aqueous dispersion of the active substance is obtained.

An aerosol composition according to the invention is obtained in the usual manner by incorporating the active substance, if desired in a solvent, in a volatile liquid to be used as a propellant gas, for example a mixture of chlorine-fluorine-derivatives of methane and ethane, a mixture of lower hydrocarbons, dimethylether, or gases like $CO_2$, $N_2$ or $N_2O$.

Smoke generating candles or smoke generating powders may also be employed. These are compositions which while burning can develop a pesticidal smoke. These compositions are obtained by taking up the active substance in a combustible mixture which, for example, may comprise as a fuel, a sugar or a wood, preferably in the ground form, a substance to maintain combustion, for example ammonium nitrate or potassium chlorate, and furthermore a substance to delay combustion for example, kaolin, bentonite and/or colloidal silicic acid.

In addition to the above-mentioned ingredients, the compositions according to the invention may also contain other substances known for use in this kind of compositions.

For example, a lubricant, for example calcium stearate or magnesium stearate, may be added to a dispersible powder or to a mixture to be granulated.

Known pesticidal compounds may also be incorporated in the compositions of the invention, such as nematicides, insecticides and fungicides. As a result of this the activity spectrum of the composition is wider and synergism may occur.

In addition bird-deterrents may be added.

The following known insecticidal and fungicidal compounds are to be considered for use in such combination compositions.

Insecticides in particular larvicides, ovicides and nematicides, for example:
1. dinitrophenols, for example 2-methyl-4,6-dinitrophenol
2. benzoylurea derivatives, for example N-(2,6-difluorobenzoyl)-N'-(4-chlorophenyl)urea.

Fungicides, for example:
1. organic tin compounds, for example triphenyl tin hydroxide and triphenyl tin acetate;
2. alkylenebisdithiocarbamates, for example, zinc ethylenebisdithiocarbamate and manganese ethylenebisdithiocarbamate;
3. 1-acyl- or 1-carbamoyl-N-benzimidazole (-2) carbamates and 1,2-bis(3-alkoxycarbonyl-2-thiureido)benzene;
4. carboxanilides, for example 5,6-dihydro-2-methyl-1,4-oxathiin-3-carboxanilides, with methyl-substituted 5,6-dihydro-4H-pyran-3-carboxanilide and with methyl-substituted furane-3-carboxanilide, and in addition 2,4-dinitro-6-(2-octyl)phenyl crotonate, 1-[(bis(dimethylamino)phosphoryl]-3-phenyl-5-amino-1,2,4-triazole, N-trichloromethylthiophthalimine, N-trichloromethylthiotetrahydrophthalimide, N-(1,1,2,2-tetrachloroethylthio)-tetrahydrophthalimide, N-dichlorofluoromethylthio-N-phenyl-N,N'-dimethylsulphamide, tetrachloroisophthalonitrile, 2-(4'-thiazolyl)benzimidazole, 5-butyl-2-ethylamino-6-methylpyrimidine-4-yl-dimethylsulphamate, 1-(4-chlorophenoxy)-3,3-dimethyl-1(1,2,4-triazole-1-yl)-2-butanone, α-(2-chlorophenyl)-α-(4-chlorophenyl)-5-pyrimidine methanol, 1-(isopropylcarbamoyl)-3-(3,5-dichlorophenyl)hydantoin, N-(1,1,2,2-tetrachloroethylthio)4-cyclohexene-1,2-carboximide, N-trichloromethylmercapto-4-cyclohexene-1,2-dicarboximide, and N-tridecyl-2,6-dimethylmorpholine.

The dosage of the composition according to the invention desired for application will depend on such factors as the form of composition, the type of crop to be protected, the kind of micro-organisms against which the crop is to be protected, the method of application, and in the case of soil application, the weather conditions.

In general, favourable results in soil application are achieved when the soil is treated with a composition according to the invention, in a dosage of 2–100 kg of active substance per ha.

When applied to the seed itself a dosage is preferred which corresponds to 100–600 mg of 2-cyano-5-nitro-thiazole per kg of seed.

The invention will now be described in greater detail with reference to the following specific examples. The powdered compositions used in said examples are obtained by intimately mixing the compounds to be tested in a concentration of from 10 to 25% with kaolin, talcum or dolomite.

EXAMPLE 1

Test on activity against Pythium spp.; soil treatment.

Soil infested with Pythium spp. is mixed with a composition of the compounds to be tested. Because Pythium spp. develop abundantly in the soil on maize grains, maize grains are added to the soil ("trapping"). After 4 days at 20° C. the maize grains are rinsed with tap water and placed in an artificial culture medium consisting of 2% of Bacto agar in water. After an incubation time of 24 hours at 23° C. it is investigated whether the mould has developed and, if so, to what extent. In the following table the extent of mold development is indicated numerically. Pythium spp. have developed normally that is abundantly, on maize grains which are kept in untreated soil, this normal development is denoted arbitrarily by 100 (control).

| Compound | Dosage in mg/l of soil | Development of Pythium spp. |
|---|---|---|
| 2-cyano-5-nitro-thiazole | 30 | 0 |
|  | 10 | 20 |
| 2-carbonamide-5-nitro-thiazole (known) | 30 | 7 |
|  | 10 | 86 |
| control | — | 100 |

EXAMPLE 2

Test on activity against Rhizoctonia solani; soil treatment.

Soil infested with Rhizoctonia solani is mixed with a composition of the compounds to be tested, after which flax stems ("trapping material") are added to the soil. After 4 days at 20° C. the flax stems are rinsed with water and placed in a culture medium as described in example 1. In the same manner as in example 1 it is established after an incubation period how the mould has developed. The results are recorded in the table below in which again a normal, that is an abundant developement, is evaluated by 100.

| Compound | Dosage in mg/l of soil | Development of Rhiz. solani |
|---|---|---|
| 2-cyano-5-nitro-thiazole | 30 | 0 |
|  | 10 | 0 |
|  | 3 | 9 |
| 2-carbonamide-5-nitro-thiazole (known) | 30 | 16 |
|  | 10 | 68 |
| control | — | 100 |

EXAMPLE 3

Test on activity against Pythium spp.; seed treatment.

Beet seed is treated with a composition of the compound to be tested and is then sowed in containers having soil which is heavily infested with Pythium spp. After 3 weeks in a hot-house at 18°–25° C. and a relative humidity of 70–100%, the coming up of healthy seedlings is examined. The result is recorded below.

| Compound | Dosage in g/kg of seed | percentage germinated healthy seedlings |
| --- | --- | --- |
| 2-cyano-5-nitro-thiazole | 1.2 | 88 |
| | 0.6 | 64 |
| | 0.3 | 23 |
| 2-carbonamide-5-nitro-thiazole (known) | 1.2 | 21 |
| | 0.6 | 22 |
| | 0.3 | 9 |
| control | — | 14 |

EXAMPLE 4

Test on activity against Fusarium nivale; seed treatment.

Wheat seed heavily infested with Fusarium nivale is treated with a composition of 2-cyano-5-nitro-thiazole, and then sowed in the field. After germination the number of seedlings per plot is determined. The coming up of untreated wheat seed serves as a control and is fixed arbitrarily at 100.

| Dosage in mg per kg of seed | Average number of seedlings |
| --- | --- |
| 600 | 135 |
| 450 | 137 |
| 300 | 121 |
| 150 | 120 |
| 0 (control) | 100 |

EXAMPLE 5

Test on activity against Pyrenophora graminea; seed treatment.

Barley seed heavily infested with Pyrenophora graminea is treated with a composition of 2-cyano-5-nitro-thiazole and then sowed in the field. In the flowering season the number of deseased plants is determined with reference to leaf and spike symptoms.

| Dosage in mg per kg of seed | percentage of diseased plants per plot |
| --- | --- |
| 600 | 0.5 |
| 450 | 0.2 |
| 300 | 0.2 |
| 150 | 0.0 |
| 0 (control) | 23.2 |

EXAMPLE 6

Test on activity against Ustilago avenae; seed treatment.

Oats seed heavily infested with Ustilago avenae is treated with a composition of 2-cyano-5-nitro-thiazole and then sowed in the field. After spike formation the number of sick plants is determined with reference to spike symptoms.

| Dosage in mg per kg of seed | percentage of diseased plants per plot |
| --- | --- |
| 600 | 0.0 |
| 450 | 0.0 |
| 300 | 0.0 |
| 150 | 0.0 |
| 0 (control) | 12.4 |

EXAMPLE 7

Test on activity against Tilletia caries; seed treatment.

Wheat seed heavily infested with Tilletia caries is treated with a composition of 2-cyano-5-nitro-thiazole and then sowed in the field. When the crop has ripened, the number of sick spikes per plot is determined.

| Dosage in mg per kg of seed | percentage of sick spikes per plot |
| --- | --- |
| 600 | 0.0 |
| 300 | 2.0 |
| 150 | 2.0 |
| 0 (control) | 11.0 |

EXAMPLE 8

Test on activity against Phoma betae; seed treatment.

Beet seed heavily infested with Phoma betae is treated with a composition of 2-cyano-5-nitro-thiazole and then sowed in the field. After coming up the number of germinated and healthy plants per plot is determined. As in example 4 the germination of untreated beet seed, (control) is fixed arbitrarily at 100.

| Dosage in mg per kg of seed | Number of healthy plants |
| --- | --- |
| 1200 | 123 |
| 600 | 110 |
| 300 | 117 |
| 0 (control) | 100 |

What is claimed is:

1. A composition for the protection of plants from soil borne or seed borne plant harmful fungi comprising a fungicidial effective amount of 2-cyano-5-nitro-thiazole and an inert carrier therefor.

2. A method of protecting plants from soil borne fungi comprising contacting the soil destined for the sowing or planting of said plants with the composition of claim 1 in a dosage of from 2 to 100 kg of the thiazole compound per hectare.

3. A method of protecting plants from seed borne fungi comprising contacting said seed with the composition of claim 1 in a dosage of from 100 to 600 mg. of the thiazole compound per kg of seed.

* * * * *